United States Patent [19]

Hoshino et al.

[11] Patent Number: 4,960,695

[45] Date of Patent: Oct. 2, 1990

[54] FERMENTATION PROCESS TO PRODUCE 2-KETO-L-GLUONIC ACID

[75] Inventors: Tatsuo Hoshino, Kamakura; Setsuko Nomura, Fujisawa; Teruhide Sugisawa, Yokohama, all of Japan

[73] Assignee: Hoffmann-La Roche Inc., Nutley, N.J.

[21] Appl. No.: 412,758

[22] Filed: Sep. 26, 1989

[30] Foreign Application Priority Data

Sep. 30, 1988 [EP] European Pat. Off. ........... 88116156

[51] Int. Cl.$^5$ .......................... C12P 7/60; C12P 39/00; C12R 1/645; C12R 1/01
[52] U.S. Cl. ..................................... 435/42; 435/138; 435/822; 435/911; 435/921; 435/924; 435/930; 435/941; 435/942; 435/944
[58] Field of Search ................. 435/42, 138, 941, 942, 435/944, 924, 911, 938, 930, 921, 822

[56] References Cited

U.S. PATENT DOCUMENTS 4,696,897 9/1987 Sonoyama et al. .................... 435/42

FOREIGN PATENT DOCUMENTS

| 0213591 | 3/1987 | European Pat. Off. ............ 435/138 |
| 0221707 | 5/1987 | European Pat. Off. ............ 435/138 |
| 0278447 | 8/1988 | European Pat. Off. ............. 435/42 |
| 2530861 | 7/1975 | Fed. Rep. of Germany ........ 435/42 |

*Primary Examiner*—Herbert J. Lilling
*Attorney, Agent, or Firm*—George M. Gould; Bernard S. Leon; William H. Epstein

[57] ABSTRACT

A process of producing 2-keto-L-gulonic acid by fermentative conversion of L-sorbose utilizing a fermentation system composed of component produced from a microorganism having the identifying characteristics of strain DSM No. 4025 and a yeast component.

30 Claims, No Drawings

FERMENTATION PROCESS TO PRODUCE 2-KETO-L-GLUONIC ACID

BACKGROUND OF THE INVENTION

2-Keto-L-gulonic acid is an important intermediate for the production of L-ascorbic acid. This compound can be converted to ascorbic acid according to the well-known Reichstein method.

The fermentative production of 2-keto-L-gulonic acid from D-sorbitol or L-sorbose is known. For example. Japanese Patent Publication No. 40154/1976 discloses the production of 2-keto-L-gulonic acid from D-sorbitol by means of microorganisms of the genus Acetobacter. Bacterium or Pseudomonas, which are capable of oxidizing D-sorbitol under aerobic conditions, thus producing 2-keto-L-gulonic acid. The yields obtained by this process are however, rather low, namely less than 6 g/1.

According to another known process, which is disclosed in "Acta Microbiologica Sinica" 21(2), 185–191, (1981), 2-keto-L-gulonic acid can be produced from L-sorbose by means of a mixed culture of microorganisms composed of *Pseudomonas striata* and *Gluconobacter oxydans*, the yield being 30 g/1 when starting from a concentration of 70 g/1 of L-sorbose, and 37 g/1 when starting from a concentration of 100 g/1 of L-sorbose.

European Patent Publication No. 0221 707 discloses the production of 2-keto-L-gulonic acid from L-sorbose by means of *Pseudogluconobacter saccharoketogenes* with and without concomitant bacteria. However, the yield of this known process by means of *Pseudogluconobacter saccharoketogenes* per se is at most 55.3–87.6 g/1 (conversion ratio: 34.2–54.1%) (See: page 13, Table 4 of European Patent Publication No. 0221 707).

Furthermore, European Patent Publication No. 0278447 discloses a process for the production of 2-keto-L-gulonic acid from L-sorbose by means of a mixed culture of microorganisms, one of which having the identifying characteristics of DSM No. 4025 and the other one having the identifying characteristics of DSM No. 4026 (a *Bacillus megaterium* strain). While the microorganism having the identifying characteristics of DSM No. 4025 particularly OSM No. 4025 itself has, as such, substantially no ability to grow and produce 2-keto-L-gulonic acid, the mixed culture, containing as the second component a *Bacillus megaterium* microorganism, does grow and does produce 2-keto-L-gulonic acid in yields of 40 g/1 and more. Thus, the presence of the second microorganism component (*Bacillus megaterium*) was considered to be essential for the operability of the process disclosed in the European Patent Publication No. 0278447.

SUMMARY OF THE INVENTION

The present invention is based on the surprising finding, that it is possible to produce 2-keto-L-gulonic acid in high yields from L-sorbose using a microorganism having the identifying characteristics of strain DSM No. 4025 without the necessity of concomitantly using another microorganism, i.e. *Bacillus megaterium*. The microorganisms utilized in accordance with this invention have the property of not being able to substantially convert L-sorbose to 2-keto-L-gulonic acid.

DETAILED DESCRIPTION

The present invention is thus directed to a process for producing 2-keto-L-gulonic acid by fermentative conversion of L-sorbose using a microorganism having the identifying characteristics of strain DSM No. 4025 and having, as such, substantially no ability to grow and produce 2-keto-L-gulonic acid, which process is characterized in that a pure culture of said microorganism is used and that the fermentation is carried out in the presence of yeast or a yeast product as a medium component.

According to the present invention, it is possible to produce 2-keto-L-gulonic acid from L-sorbose at a substantially improved yield, namely a yield of more than 72 g/1 (conversion ratio: 93.7%) when starting from a L-sorbose concentration of 80 g/1, and even more than 100 g/1 (conversion ratio: 92.8%) when starting from a L-sorbose concentration of 100 g/1 and at higher yields when starting from higher concentrations. Conversion ratio is calculated based on the amounts of 2-keto-L-gulonic acid produced and L-sorbose consumed.

The microorganisms used in the present invention have the identifying characteristics of strain DSM No. 4025 and has as such, substantially no ability to grow and to produce 2-keto-L-gulonic acid. The main identifying characteristics are:

negative oxidase test; ethanol is oxidized to acetic acid; D-glucose is oxidized to D-gluconic acid and 2-keto-D-gluconic acid; ketogenesis of polyalcohols; dihydroxyacetone is not substantially produced from glycerol; 2-keto-D-glucaric acid is produced from D-sorbitol and D-glucaric acid, but not from D-glucose. D-fructose, D-gluconic acid. D-mannitol or 2-keto-D-gluconic acid; polymorphic, apparently no flagella; brown pigment is produced from fructose; good growth when co-cultured in the presence of *Bacillus megaterium* or a cell extract thereof; streptomycin sensitive.

In the present invention, a pure or homogeneous culture of the microorganism is used. The term "a pure culture" or homogeneous culture of the microorganism means a culture which contains the microorganism only, without any other concomitant microorganisms, such as *Pseudomonas striata* and *Bacillus megaterium*, thereby differing from the cultures used in the processes disclosed in "Acta Microbiolgica Sinica" 21 (2), 185–191 (1981) as mentioned above, and in European Patent Publication No. 278 447, where the use of mixed cultures is disclosed.

A specific and preferred microorganism strain has been deposited at the Deutsche Sammlung von Mikroorganismen in Gottingen under DSM No. 4025 on March 17, 1987 under the Budapest Treaty (the present address of this institute is: Deutsche Sammlung von Mikroorganismen und Zellkulturen GmbH, Mascheroder Weg lb, D-3300 Braunschweig, Federal Republic of Germany).

The cells of the DSM No. 4025 microorganism are rod-shaped with rounded ends. The diameter of a cell of the microorganism is, on an average about 0.3–0.6 $\mu$m, its length about 0.9–1.6 $\mu$m, mainly 1–1.5 $\mu$m.

In the preferable embodiment of the present invention, the production of 2-keto-L-gulonic acid is effected by cultivating the microorganism referred to above in a medium containing L-sorbose and yeast or a yeast product as well as appropriate nutrients. Alternatively, this process may be carried out by cultivating the microorganism in the above mentioned medium and, thereafter, bringing the whole cells collected from the culture or its cell-free extract into contact with L-sorbose.

In carrying out the reaction of this invention, any microorganism having the identifying characteristics of strain DSM No. 4025, can be utilized. Such strains which have the identifying characteristics of strain PSM No. 4025 include appropriate subculture, functional equivalent variant or mutant thereof which have the power to transform, in combination with any yeast or yeast product L-sorbose into 2 keto-L-gulonic acid can be utilized. Any conventional yeast or yeast product can be utilized. The yeast products which are utilized in accordance with this invention can be any component obtained from the yeast which has the growth promoting properties of the yeast from which it is obtained.

The yeast used in the present invention includes any yeast belonging to the subclass Ascomycetes. Particularly to the genus Saccharomyces, such as *Saccharomyces cerevisiae* (baker's yeast). *Saccharomyces carlsbergensis* (*Saccharomyces uvarum*) (brewer's yeast) or *Saccharomyces sake*, or to the genus Schizosaccharomyces, such as *Schizosaccharomyces pombe*, or to the genus Pichia, such as *Pichia membranaefaciens*, or to the genus Hansenula, such as *Hansenula anomala*, or yeast belonging to the subclass Hyphomycetes, particularly to the genus Candida, such as *Candida tropicalis* or *Candida utilis*, or to the genus Torulopsis, such as *Torulopsis versatilis* (*Candida versatilis*) or *Torulopsis holmii* (*Candida holmii*), or a yeast product thereof. The yeasts mentioned above are freely available from depositories or from commercial sources. Thus, the yeasts mentioned above belonging to the species *Saccharomyces cerevisiae* can be purchased from private companies for instance as baker's yeast. For example, the following baker's yeast can be purchased from the following companies:

Oriental yeast (Oriental Yeast Co.)
Kaneka yeast (Kanegafuchi Chemical Industry Co.)
Daiya yeast (Kyowa Hakko Kogyo Co.)
Sankyo yeast (Sankyo Co.)
Chuetsu yeast (Chuetsu Yeast Co.)
Yeast 45 (Toyo Jozo Co.)
Nitten yeast (Nippon Beet-Sugar Co )

Moreover, the following yeasts can be also purchased from IFO (Institute for Fermentation, Osaka. Japan),

| | | |
|---|---|---|
| *Saccharomyces cerevisiae* | IFO | 1234 |
| *Saccharomyces carlsbergensis* | IFO | 0565 |
| (*Saccharomyces uvarum*) | | |
| *Saccharomyces sake* | IFO | 0309 |
| *Candida tropicalis* | IFO | 1400 |
| *Candida utilis* | IFO | 0396 |
| *Torulopsis versatilis* | IFO | 10056 |
| (*Candida versatilis*) | | |
| *Torulopsis holmii* | IFO | 1629 |
| (*Candida holmii*) | | |
| *Schizosaccharomyces pombe* | IFO | 0362 |
| *Pichia membranaefaciens* | IFO | 10215 |
| *Hansenula anomala* | IFO | 1021 |

It is essential that the yeast used in the present process contains growth factors for the microorganisms used according to the present invention. The common properties of said growth factors are thermal stability and solubility in water.

The yeast or yeast products used in the present invention include so-called "fresh yeast", dry yeast, yeast extract and the like. The term "fresh yeast" herein means yeast cells just collected from the culture broth by means of centrifugation, filtration and the like. Baker's yeast as commercialized in conventional form is a specific representative of such "fresh yeast". However, fresh yeast, such as baker's yeast. after having been heated at e.g. 121° C. can also be used advantageously in the process of the present invention. As a matter of fact, the use of sterilized yeast is preferred in view of the fact that live yeast would metabolize part of the L-sorbose used as substrate and thereby reduce the 2-KGA yield. Thus, the use of sterilized yeast, such as sterilized baker's yeast, is a highly preferred embodiment of the present invention.

Where the microorganism is cultured in a nutrient medium containing L-sorbose as well as yeast or a yeast product, the microorganism is conveniently cultured in an aqueous medium under aerobic conditions. However, any conventional fermentation conditions can be utilized in carrying out the process of this invention.

The concentration of the above yeast according to the present invention is preferably from about 5 g/1 to about 150 g/1 by wet weight in the medium, preferably from about 20 g/1 to about 100 q/1 by wet weight in the medium. The instant fermentation process may be carried out at a pH between about 4,0 and 9.0, preferably between about 6.0 and 8.0. A preferred temperature range for carrying out the instant fermentation process is between about 13 and 36° C. More preferably, the instant fermentation process is carried out at a temperature between about 18 and 33° C. While the fermentation period may vary, depending on pH, temperature and nutrient medium used, usually 2 to 5 days will bring about faVorable results. The concentration of the L-sorbose used as starting material in the instant process may vary between about 20 and 250 g/1. Preferably between about 50 and about 200 g/1.

The culture medium used in the instant fermentation process usually contains such nutrients for the microorganisms as assimilable carbon sources, digestible nitrogen sources and inorganic substances, vitamins, trace elements and other growth promoting factors. In addition to L-sorbose used as starting material in the instant process, other substances which are carbon sources may also be added, such as glycerol, D-glucose, D-mannitol, D-fructose, D-arabitol and the like.

Various organic or inorganic substances may also be used as nitrogen sources in the instant process, such as meat-extract, peptone, casein, corn steep liquor, urea, amino acidsnitrates, ammonium salts and the like. As inorganic substances, magnesium sulfate, potassium phosphate, ferrous and ferric chlorides, calcium carbonate and the like may be used.

In the case where pregrown whole cells collected from the culture are used, the cultivation of the microorganism is carried out under the same or similar conditions as described above. These whole cells are used in an aqueous medium under aerobic conditions, no additional nutrients (in addition to the L-sorbose used as starting material) are necessary.

In case where cell-free extracts from the culture are used, these extracts are added to the substrate in an aqueous medium and are used in the conversion of L-sorbose to 2-keto-L-gulonic acid under aerobic conditions in a manner similar to that set forth above, no additional nutrients being necessary also in this case.

The 2-keto-L-gulonic acid obtained according to the present process can be isolated from the reaction mixture, e.g. by the formation of a salt or by using differences in properties between the product and the surrounding impurities, such as solubility, absorbability and distribution coefficient between the solvents. Adsorption. e.g. on ion exchange resins constitutes a convenient means for isolating the product. The thus obtained product may further be purified in a conventional manner. e.g. by recrystallization or chromatography.

Alternatively, the reaction mixture can be used directly for conversion to L-ascorbic acid by esterification, followed by enolization and lactonization.

The present invention is illustrated by the following Examples:

EXAMPLE 1

A seed culture medium containing L-sorbose 8.0% separately sterilized), glycerol 0.05%, $MgSO_4 \cdot 7H_2O$ 0.25%, corn steep liquor 1.75%, yeast extract B-II (Oriental Yeast Co.) 0.25%, $CaCO_3$ 0.5% and urea 0.5% (separately sterilized) (pH 7.0 before sterilization) was distributed into test tube (5 ml each) and sterilized at 121° C. for 20 minutes. Into this seed culture medium, one loopful amount of the cells of microorganism DSM No. 4025 grown on a slant culture medium containing glycerol 3.0%, $MgSO_4 \cdot 7H_2O$ 0.25%, corn steep liquor 1.75% yeast extracts B-II 0.25%. $CaCO_3$ 0.5%, urea 0.5% (separately sterilized) and agar 2.0% (pH 7.0 before sterilization at 27° C. for four days was inoculated and incubated at 30° C. for 24 hours. The resulting seed culture was inoculated into 50 ml of the same seed culture medium as described above in a 500 ml Erlenmeyer flask and incubated for 24 hours at 30° C. The basal production medium (50 ml) containing L-sorbose 8.0% (sterilized separately), glycerol 0.05%, urea 1.0% (sterilized separately), $MgSO_4 \cdot 7$ $H_2O$ 0.25%, $CaCO_3$ 1.5% and corn steep liquor 3.0% was supplemented with yeast extract B-II 0.5% and/or baker's yeast (Oriental Yeast Co. 5% in a 500 ml Erlenmeyer flask and sterilized at 121° C for 20 minutes. Into these production media, 5 ml each of the seed culture as prepared above was added and incubated at 30° C. for 4 days at an agitation speed of 180 rpm.

By high performance liquid chromatographic analysis. 2-keto-L-gulonic acid (2-KGA) content in the cultured broth supplemented with baker's yeast was determined to be 72 1 g/l (conversion rate: 93.7%). On the other hand 2-KGA content of the broths supplemented with yeast extract B-II and yeast extract B-II/baker's yeast were 57.1 (conversion rate: 88.8%) and 64.9 g/l (conversion rate; 94.4%), respectively.

EXAMPLE 2

A seed culture medium containing L-sorbose 8.0% (separately sterilized). glycerol 0.05%, $MgSO_4 \cdot 7H_2O$ 0.25%, corn steep liquor 1.75%, baker's yeast 5.0%, $CaCO_3$ 0.5% and urea 0.5% separately sterilized) (pH 7.0 before sterilization) was distributed into test tubes (5 ml each) and sterilized at 121° C. for 20 minutes. Into this seed culture medium, one loopful amount of the cells of microorganism DSM No. 4025 grown on a slant culture medium containing D-mannitol 5.0%. $MgSO_4 \cdot 7H_2O$ 0.25%, corn steep liquor 1.75%, baker's yeast 0.25%, $CaCO_3$ 0.5%, urea 0.5% (separately sterilized) and agar 2.0%, (pH 7.0 before sterilization) at 27° C for four days was inoculated and incubated at 30° C for 24 hours. The resulting seed culture was inoculated into 50 ml of the same seed culture medium as described above in a 500 ml Erlenmeyer flask and incubated for 24 hours at 30° C. The basal production medium (50 ml) containing L-sorbose 10.0% (sterilized separately), glycerol 0.05%, urea 1.6% (sterilized separately). $MgSO_4 7H_2O$ 0.25%, $CaCO_3$ 1.5% and corn steep liquor 3.0% was supplemented with the yeasts as listed in Table 1 in 500 ml Erlenmeyer flasks and sterilized for 20 minutes at 121° C. Into these production media, 5 ml each of the seed culture as prepared above was added and incubated at 30° C. for 4 days with the agitation speed of 180 rpm.

2-KGA values of flasks of various conditions are shown in Table 1.

TABLE 1

Effect of various yeasts used as medium component on 2-KGA production

| Yeasts | Source | Amount % | 2-KGA (g/l) | Remaining L-sorbose (g/l) | Cell growth |
|---|---|---|---|---|---|
| Yeast extract B-II | Oriental | 0.25 | 68.5 | 31.1 | + |
|  |  | 0.5 | 74.1 | 25.3 | + |
| Yeast powder HG (dry yeast) | Oriental | 0.25 | 75.6 | 23.0 | + |
|  |  | 0.5 | 79.4 | 20.9 | + |
| Yesta 20A (Dry yeast) | Bovril[1] | 0.25 | 84.2 | 15.3 | ++ |
|  |  | 0.5 | 87.3 | 12.0 | ++ |
| Saf-instant (dry yeast) | S. I. Le-saffre[2] | 0.25 | 81.1 | 17.4 | ++ |
|  |  | 0.5 | 86.0 | 13.8 | ++ |
| Oriental dry yeast | Oriental | 0.25 | 76.8 | 21.3 | ++ |
|  |  | 0.5 | 86.5 | 13.7 | ++ |
| Baker's yeast (S. cerevisiae) | Oriental | 5.0 | 93.5 | 8.9 | +++ |
|  |  | 6.25 | 97.2 | 4.4 | +++ |
| None |  | 0 | 4.0 | 93.0 | ± |

Degree of cell growth: ± bad → +++ good
[1]Saccharomyces cerevisiae available from Oriental Yeast Co.
[2]Baker's yeast

EXAMPLE 3

In the same manner as described in Example 2, the seed culture was prepared, inoculated into 50 ml of the production medium containing L-sorbose 9.0% (separately sterilized), glycerol 0.05%, corn steep liquor 3.0%, urea 1.4% (separately sterilized), baker's yeast 5.6%, $MgSO_4 \cdot 7H_2O$, 0.25% and $CaCO_3$ 1.5% in a 500 ml Erlenmeyer flask and incubated at 30° C. for 1 days at an agitation speed of 180 rpm.

As a result, 89.0 g/l (conversion rate: 91.8%) of 2-KGA was produced.

EXAMPLE 4

In the same manner as described in Example 2, the seed culture was prepared, inoculated into 50 ml of the production medium containing L-sorbose 10.0% (separately sterilized). glycerol 0.05%, corn steep liquor 3.0%, urea 1.6% (separately sterilized), baker's yeast 6.25%, $MgSO_4 \cdot 7H_2O$ 0.25% and $CaCO_3$ 1.5% in a 500 ml Erlenmeyer flask and incubated at 30° C. for 4 days at an agitation speed of 180 rpm.

As a result 97.2 g/l (conversion rate: 90.2%) of 2-KGA was produced.

EXAMPLE 5

In the same manner as described in Example 2 the seed culture was prepared, inoculated into 50 ml of the production medium containing L-sorbose 12.0% separately sterilized), glycerol 0.05%. corn steep liquor 3.0%, urea 1.9% (separately sterilized), baker's yeast 7.5%, $MgSO_4$ $7H_2O$, 0.25% and $CaCO_3$ 1.5% in a 500 ml Erlenmeyer flask and incubated at 30° C. for 4 days at an agitation speed of 180 rpm.

As a result, 98.5 g/l (conversion rate: 89.4%) of 2-KGA was produced.

EXAMPLE 6

In the same manner as described in Example 2, the seed culture was prepared, inoculated into 50 ml of the production medium containing L-sorbose 8.0% (separately sterilized), glycerol 0.05%, corn steep liquor 3.0%, urea 1.25% (separately sterilized), $MgSO_4 \cdot 7H_2O$ 0.25%, $CaCO_3$ 1.5% and 2 to 5% of baker's yeast, and incubated at 30° C. for 3 to 4 days.

As shown in Table 2, 82.6 g/l (conversion rate: 95.8%) of 2-KGA was produced in 4 days incubation in the medium supplemented with 4% of baker's yeast.

TABLE 2

| | Effect of concentration of baker's yeast on 2-KGA production | | |
|---|---|---|---|
| | 2-KGA produced (g/l) | | |
| Baker's yeast | 3 days | 4 days | (Conversion: %) |
| 2 | 75.1 | 77.5 | (95.4) |
| 3 | 80.6 | 81.3 | (94.3) |
| 4 | 81.6 | 82.6 | (95.8) |
| 5 | 81.8 | 82.6 | (95.8) |

EXAMPLE 7

In the same manner as described in Example 2, 200 ml of the seed culture was prepared. Into a 3 l jar fermentor, 1.2 l of basal medium containing glycerol 0.05%, corn steep liquor 3.0%, baker's yeast 5.0% and $MgSO_4 \cdot 7H_2O$ 0.25% to be made up to 2.0 l, was added and sterilized at 121° C. for 20 minutes. L-sorbose 8% (final concentration) and urea 1.25% (final concentration) were separately sterilized and added into the fermentor. After the inoculation by the seed culture, the culture volume was adjusted to 2 liters by addition of sterilized water. The fermentation was carried out at 30° C. 800 rpm for agitation an 1 liter/minute for aeration. The pH of the culture was maintained at 7.0 by 4N of $Na_2CO_3$.

In 40 hours fermentation, 84 g/l (conversion rate: 97.4%) of 2-KGA was produced.

EXAMPLE 8

In the same manner as described in Example 7, 3 l jar fermentation was carried out in a medium containing L-sorbose 10.0%, urea 1.6%, glycerol 0.05%, $MgSO_4 \cdot 7H_2O$ 0.25%, corn steep liquor 3.0% and baker's yeast 6.25%.

As a result, 100.0 g/l (conversion rate: 92.8%) of 2-KGA was produced in 50-hours fermentation.

EXAMPLE 9

In the same manner as described in Example 7, 3 l jar fermentation was carried out in a medium containing L-sorbose 12.0%, urea 1.9%, glycerol 0.05%. $MgSO_4 \cdot 7H_2O$ 0.25%, corn steep liquor 3.0% and baker's yeast 7.5%.

As a result, 98.0 g/l (conversion rate! 92.3%) of 2-KGA was produced in 75-hours fermentation. 21.5 g/l of L-sorbose remained unconsumed.

EXAMPLE 10

A 3 l jar fermentation was started in the same manner as described in Example 7. On the other hand. 80 g of L-sorbose was solubilized in 400 ml of water and sterilized at 121° C for 20 minutes and fed continuously into the fermentor at a feeding rate of about 11 ml/min from 6 to 42 hours of fermentation. After the termination of L-sorbose feeding, the fermentation was continued for further 25 hours. The total fermentation period was 67 hours. In the cultured broth (2.6 l), 95 g/l of 2-KGA was produced. Totally, 247 g of 2-KGA was produced from 240 g of L-sorbose. Molar conversion rate: 95.5%.

EXAMPLE 10

A 3 l jar fermentation was started in the same manner as described in Example 7. On the other hand. 120 g L-sorbose was solubilized in 400 ml of water and sterilized at 121° C. for 20 minutes and fed continuously into the fermentor at a feeding rate of about 11 ml/min from 6 hours to 42 hours of fermentation. After the termination of L-sorbose feeding, the fermentation was continued for further 35 hours. The total fermentation period was 77 hours. In the cultured broth (2.7 l), 104 g/l of 2-KGA was produced. Totally, 280.8 g of 2-KGA was produced from 280 g of L-sorbose. Molar conversion rate: 93.1%.

EXAMPLE 12

A 3 l jar fermentation was started in the same manner as described in Example 7. On the other hand. 160 g of L-sorbose was solubilized in 400 ml of water and sterilized at 121° C. for 20 minutes and fed continuously into the fermentor at a feeding rate of about 11 ml/min from 6 hours to 42 hours fermentation continuously. After the termination of L-sorbose feeding, the fermentation was continued for further 49 hours. The total fermentation period was 91 hours. In the cultured broth (2.7 l), 110 g/l of 2-KGA was produced. Totally, 297 g of 2-KGA Was produced from 320 g of L-sorbose. Molar conversion rate: 86.1%.

EXAMPLE 13

In the same manner as described in Example 2, the seed culture was prepared. 5 ml each of the seed culture was inoculated into 50 ml of the production media containing L-sorbose 10% (sterilized separately), glycerol 0.05%, urea 1.6% (sterilized separately), $MgSO_4 \cdot 7H_2O$ 0.25%, corn steep liquor 3.0%, $CaCO_3$ 1.5% and baker's yeast from various suppliers as listed in Table 3, 6.25% in 500 ml of Erlenmeyer flask. The fermentation was carried out at 30° C. for 4 days at an agitation speed of 180 rpm. The results are shown in Table 3.

TABLE 3

| Effect of various baker's yeasts on 2-KGA production | | | |
|---|---|---|---|
| Type of baker's yeast | 2-KGA (g/l) | (Conversion) (%) | Remaining L-sorbose (g/l) |
| Oriental yeast | 97.2 | (94.4) | 4.4 |
| Kaneka yeast | 91.4 | (90.5) | 6.3 |
| Daiya yeast | 94.6 | (92.3) | 4.9 |
| Sankyo yeast | 87.4 | (88.7) | 8.6 |
| Chuhetsu yeast | 93.7 | (92.2) | 5.7 |
| Yeast 45 | 90.1 | (89.5) | 6.6 |
| Nitten yeast | 97.2 | (93.8) | 3.8 |

EXAMPLE 14

The basal production medium (5 ml). which contained L-sorbose 8% (sterilized separately), glycerol 0.5%, urea 1.25% (sterilized separately), $MgSO_4$ 0.25%, $CaCO_3$ 1.5% and corn steep liquor 3.0%. (pH 7.5 before sterilization), was supplemented with yeast cells (5% wet weight/volume), distributed in test tubes (1.8×20 cm) and sterilized at 121° C. for 20 minutes. As the yeast cells cultures of *Saccharomyces sake* IFO 0309, *Schizocchqromyces pombe* IFO 0362. *Saccharomyces* carlsbergensis IFO 0565, *Saccharomyces cerevisiae* IFO 1234. *Candida utilis* IFO 0396, *Candida tropicalis* IFO 1400, *Torulopsis holmii* IFO 1629, *Torulopsis versatilis* IFO 10056, *Hansenula anomala* IFO 10213 and *Pichia membranaefaciens* IFO 10215 on an agar culture medium containing malt extract (Difco) 1.0%, yeast extract (Difco) 0.1%, soytone (Difco) 0.1%, glucose 1.0% and agar 2.0%, grown at 27° C. for 4 days were used. Into the production media, 0.5 ml each of the seed culture of microorganism DSM No. 4025 as prepared in the same manner as described in Example 2 was inoculated and incubated at 30° C. for 4 days.

2-KGA values of tubes in various conditions are shown in Table 4.

TABLE 4

Effect of the yeast belonging to genus Saccharomyces, Candida, Torulopsis, Hansenula and Pichia Used as medium component on 2-KGA production

| Yeasts | amount (%) | 2-KGA (g/l) | Remaining L-sorbose (g/l) |
|---|---|---|---|
| *Saccharomyces sake* IFO 0309 | 5.0 | 74.37 | 5.56 |
| *Schizosaccharomyces pombe* IFO 0362 | 5.0 | 77.99 | 1.46 |
| *Saccharomyces carlsbergensis* IFO 0565 | 5.0 | 70.82 | 2.61 |
| *Saccharomyces cerevisiae* IFO 1234 | 5.0 | 72.39 | 3.89 |
| *Candida utilis* IFO 0396 | 5.0 | 71.05 | 0 |
| *Candida tropicalis* IFO 1400 | 5.0 | 80.95 | 2.91 |
| *Torulopsis holmii* IFO 1629 | 5.0 | 72.20 | 6.32 |
| *Torulopsis versatilis* IFO 10056 | 5.0 | 78.01 | 0 |
| *Hansenula anomala* IFO 10213 | 5.0 | 75.91 | 1.97 |
| *Pichia membranaefaciens* IFO 10215 | 5.0 | 65.56 | 12.78 |

EXAMPLE 15

A seed culture medium S1 containing L-sorbose 8.0% (separately sterilized). glycerol 0.05%, $MgSO_4 \cdot 7H_2O$ 0.25%, yeast extract B-II 1.5% and $CaCO_3$ 1.5% (separately sterilized) (pH 7.0 before sterilization) was distributed into test tubes (5 ml each) and sterilized at 121° C. for 20 minutes. Into this seed culture medium, one loopful amount of the cells of *Gluconobacter oxydans* U-13 (FERM-BP No. 1269) grown on the slant culture medium was inoculated and incubated at 30° C. for 4B hours. The resulting seed culture was inoculated into 50 ml of the same seed culture medium as described above in a 500 ml Erlenmeyer flask and incubated for 48 hours at 30° C. On the other hand, another seed culture was prepared using the seed culture medium S2 containing L-sorbose 8.0%, $MgSO_4 \cdot 7H_2O$ 0.25% glycerol 0.05%, $CaCO_3$ 1.5%. urea 0.5%, corn steep liquor 1.75% and baker's yeast 5 0% in the same manner as described above. The seed cultures S1 and S2 thus prepared were inoculated into the production medium in the same manner as described in Example 2. The fermentation was carried out at 30° C. for 4 days.

The 2-KGA yield obtained was 12.8 g/l in the case of culture medium S1 and 10.2 g/l in the case of culture medium S2. This shows that *Gluconobacter oxydans* U-13 (FERM-BP No. 1269) which, as a pure culture, has ability to grow and produce 2-KGA, did not give 2-KGA in high yield in yeast-containing production media.

What is claimed is:

1. A process for producing 2-keto-L-gluconic acid comprising fermentatively converting in a nutrient medium, L-sorbose to 2-keto-L-gluconic acid by the action of fermentation system containing:
   a. a biologically homogeneous culture of a microorganism having the identifying characteristics of strain DSM No. 4025, and having substantially no ability to produce 2-keto-L-gluconic acid from L-sorbose; and
   b. a yeast or a component obtained from said yeast having the growth promoting activity of the yeast from which said component is obtained.

2. The process of claim 1 wherein the yeast belongs to the subclass Ascomycetes.

3. The process of claim 2 wherein said yeast belongs in the genus Saccharomyces.

4. The process of claim 3 wherein said yeast is *Saccharomyces cerevisiae* (baker's yeast), *Saccharomyces carlsbergensis*(*Saccharomyces uvarum*) (brewer's yeast) or *Saccharomyces sake*.

5. The process of claim 2 wherein said yeast belongs to the genus Schizosaccharomyces.

6. The process of claim 5 wherein the yeast is Schizosaccharomyces pombe.

7. The process of claim 2 wherein the yeast belongs to the genus Pichia or Hansenula.

8. The process of claim 7 wherein the yeast is *Pichia membranaefaciens* or *Hansenula anomala*.

9. The process of claim 1 wherein the yeast belongs to the subclass Hyphomycetes.

10. The process of claim 9 wherein the yeast belongs to the genus Candida or Torulopsis.

11. The process of claim 10 wherein said yeast is *Candida tropicalis, Candida utilis, Torulopsis versatilis* (*Candida versatilis*) or *Torulopsis holmii* (*Candida holmii*).

12. The process of claim 1 wherein the yeast is used at a concentration of from about 5 g/l to about 150 g/l by wet weight.

13. The process of claim 1 wherein L-sorbose is used at a concentration of from about 20 g/l to about 250 g/l.

14. The process of claim 1 wherein 2-keto-L-gulonic acid is produced in a yield of at least 72 g/l.

15. The process of wherein the fermentative conversion is carried out at pH between about 4.0 and 9.0.

16. The process according to claim 1 wherein the fermentative conversion is carried out at a temperature between about 13° C. and 36° C.

17. A process of producing 2-keto-L-gluconic acid comprising fermentatively converting, in a nutrient medium, L-sorbose to 2keto-L-gluconic acid by the action of a fermentation system containing:
   a. a cell free or whole cell extract obtained from a biologically homogeneous culture of microorganism having the identifying characteristics of strain DSM No. 4025, and having substantially no ability to produce 2-keto-gluonic acid from L-sorbose; and
   b. a yeast or component obtained therefrom having the growth promoting activity of the yeast from which said component is obtained.

18. The process of claim 17 wherein the yeast belongs to the subclass Ascomycetes.

19. The process of claim 18 wherein said yeast belongs in the genus Saccharomyces.

20. The process of claim 19 wherein said yeast is *Saccharomyces cerevisiae* (baker's yeast), *Saccharomyces carlsbergensis* (*Saccharomyces uvarum*) (brewer's yeast) or *Saccharomyces sake*.

21. The process of claim wherein said yeast belongs to the genus Schizosaccharomyces.

22. The process of claim 21 wherein the yeast is Schizosaccharom pombe.

23. The process of claim 18 wherein the yeast belongs to the genus Pichia or Hansenula.

24. The process of claim 25 wherein the yeast is *Pichia membranaefaciens* or *Hansenula anomala*.

25. The process of claim 17 wherein the yeast belongs to the subclass Hyphomycetes.

26. The process of claim 25 wherein the yeast belongs to the genus Candida or Torulopsis.

27. The process of claim 26 wherein said yeast is *Candida tropicalis, Candida utilis, Torulopsis versatilis* (*Candida versatilis*) or *Torulopsis holmii* (*Candida holmii*).

28. The process of claim 27 wherein the yeast is used at a concentration of from about 5 g/l to about 150 g/l by wet weight.

29. The process of claim 17 wherein L-sorbose is used at a concentration of from about 20 g/l to about 250 g/l.

30. The process of claim 17 wherein 2-keto-L-gulonic acid is produced in a yield of at least 72 g/l.

* * * * *

UNITED STATES PATENT AND TRADEMARK OFFICE
CERTIFICATE OF CORRECTION

PATENT NO. : 4,960,695
DATED : October 2, 1990
INVENTOR(S) : Tatsuo Hoshino, Setsuko Nomura and Teruhide Sugisawa It is certified that error appears in the above-identified patent and that said Letters Patent is hereby corrected as shown below:

Column 10, line 49,
claim 15, "The process of wherein"
should be --The process of claim 1 wherein--

Column 11, line 7,
claim 21, "The process of claim wherein"
should be--The process of claim 18 wherein--

Signed and Sealed this

Ninth Day of June, 1992

Attest:

DOUGLAS B. COMER

*Attesting Officer*    *Acting Commissioner of Patents and Trademarks*